(12) United States Patent
Święszkowski et al.

(10) Patent No.: US 11,260,148 B2
(45) Date of Patent: Mar. 1, 2022

(54) METHOD FOR MANUFACTURING BONE IMPLANTS AND BONE IMPLANT

(71) Applicant: INSTYTUT WYSOKICH CIŚNIEŃ POLSKIEJ AKADEMII NAUK, Warsaw (PL)

(72) Inventors: Wojciech Święszkowski, Warsaw (PL); Tadeusz Chudoba, Warsaw (PL); Sylwia Kuśnieruk, Warsaw (PL); Aleksandra Kędzierska, Kolonia Zawada (PL); Bartosz Woźniak, Mońki (PL); Julia Rogowska-Tylman, Warsaw (PL); Dariusz Smoleń, Jaslo (PL); Elzbieta Pietrzykowska, Lochów (PL); Witold Lojkowski, Warsaw (PL); Jacek Wojnarowicz, Jaslo (PL); Aharon Gedanken, Givataim (IL); Janis Locs, Jaunolaine (LV); Vita Zalite, Vecumnieki (LV); Mara Pilmane, Riga (LV); Ilze Salma, Riga (LV)

(73) Assignee: INSTYTUT WYSOKICH CISNIEN POLSKIEJ AKADEMII NAUK, Warsaw (PL)

( * ) Notice: Subject to any disclaimer, the term of this patent is extended or adjusted under 35 U.S.C. 154(b) by 0 days.

(21) Appl. No.: 15/571,825

(22) PCT Filed: May 5, 2016

(86) PCT No.: PCT/IB2016/052566
§ 371 (c)(1),
(2) Date: Nov. 4, 2017

(87) PCT Pub. No.: WO2016/178174
PCT Pub. Date: Nov. 10, 2016

(65) Prior Publication Data
US 2018/0311407 A1    Nov. 1, 2018

(30) Foreign Application Priority Data
May 5, 2015  (PL) .......................................... 412238

(51) Int. Cl.
*A61L 27/32*       (2006.01)
*A61L 27/56*       (2006.01)
(Continued)

(52) U.S. Cl.
CPC ............... *A61L 27/32* (2013.01); *A61L 27/10* (2013.01); *A61L 27/12* (2013.01); *A61L 27/14* (2013.01);
(Continued)

(58) Field of Classification Search
None
See application file for complete search history.

(56) References Cited

U.S. PATENT DOCUMENTS 5,626,861 A * 5/1997 Laurencin ............... A61L 27/46
                                                                424/426
8,449,603 B2 * 5/2013 Weber ................... A61L 31/088
                                                                623/1.48

FOREIGN PATENT DOCUMENTS

EP    2 298 365 A1    3/2011
EP    2298365 A1 *    3/2011    ......... A61L 27/3804
(Continued)

OTHER PUBLICATIONS

Smolen, Hydroxyapatite Nanopowder Synthesis with a Programmed Resorption Rate, Journal of Nanomaterials, vol. 2012. (Year: 2012).*
(Continued)

*Primary Examiner* — Melissa S Mercier
(74) *Attorney, Agent, or Firm* — Horst M. Kasper, Esq

(57) ABSTRACT

The method of making an implant consists on coating of a supporting structure (1) with synthetic hydroxyapatite by
(Continued)

immersing the supporting structure (1) in a suspension (3) and triggering of a cavitation in a portion of the suspension (3) being in contact with the supporting structure (1). The suspension (3) is formed by a liquid external phase, advantageously water, and internal phase, i.e. particles of synthetic hydroxyapatite having an average particle size not exceeding 100 nm and containing structural water in an amount from 2 to 6% by weight. The implant is coated with the above described hydroxyapatite subjected to cavitation and a thickness of 50 nm to 1000 nm, advantageously 50 nm to 300 nm.

10 Claims, 6 Drawing Sheets

(51) Int. Cl.
    *A61L 31/08*     (2006.01)
    *A61L 27/10*     (2006.01)
    *A61L 27/12*     (2006.01)
    *A61L 27/14*     (2006.01)
(52) U.S. Cl.
    CPC ............. *A61L 27/56* (2013.01); *A61L 31/086* (2013.01); *A61L 2400/12* (2013.01); *A61L 2420/02* (2013.01); *A61L 2430/02* (2013.01)

(56) References Cited

FOREIGN PATENT DOCUMENTS

| EP | 2 444 027 A2 | 4/2012 | |
|---|---|---|---|
| EP | 2626147 A1 * | 8/2013 | ........... G10K 15/043 |
| WO | WO 2013/112 743 A1 | 8/2013 | |

OTHER PUBLICATIONS

Athanasiou, K.A (1998). The effects of porosity on in vitro degradation of polylactic acid-polyglycolic implants used in repair of articular cartilage. (Year: 1998).*
www.science.answers.com obtained Jan. 5, 2019 (Year: 2019).*
Scapin et al. Determination of Ca/P molar ratio in Hydroxyapatite by X-ray fluorescence technique, 2015 (Year: 2015).*
Hielscher Ultrasound Technology, accessed Jan. 5, 2019 (Year: 2019).*
Athanasiou, K.A (The effects of porosity on in vitro degradation of polylactic acid-polyglycolic acid implants used in repair of articular cartilage, 1998). (Year: 1998).*
Lian et al. (Mechanical Properties of polylactic acid/beta-tricalcium phosphate composite scaffold with double channels based on three dimensional printing technique, Mar. 2014; 28(3):309-13), (Year: 2014).*
A. Kedzierska et al. European Cells and Materials, vol. 26, No. S2 Jan. 1, 2013, pp. 17-17, XP055295069, US the whole document.

* cited by examiner

METHOD FOR MANUFACTURING BONE IMPLANTS AND BONE IMPLANT

TECHNICAL FIELD

The invention regards a method of producing bone implants having a character of supporting structure at least partially coated with a synthetic hydroxyapatite and bone implants for use in orthopaedic surgery, trauma surgery (traumatology), regenerative implantology, which facilitate or accelerate the regeneration of bone tissue.

BACKGROUND ART

In medicine, particularly in orthopaedics, dentistry and traumatology, and in the treatment of bone defects caused by the removal of the tumour, implants, also known as scaffolds for bone tissue regeneration, are used in order to induce or accelerate regeneration of the bone tissues by the organism; tissue that was lost as a result of trauma, surgery of cancer removal, orthopaedic surgery, dental surgery, tooth extraction, other causes or improvement of aesthetics. For the production of such implants various kinds of synthetic biomaterials (metals, ceramics, synthetics—polymers, composites) as well as natural materials are used. They must meet a number of criteria, including no toxicity to the body, proper filling of the missing bone volume and appropriate mechanical properties. In particular, a very valuable feature of such materials is their bioresorption.

Presently, there are many treatment methods for small defects in bones, but still no solution for large tissue loss (so-called critical loss) is known. To fill the cavity and facilitate active bone regeneration an scaffold should be created (implant), both filling the space of bone loss and transferring mechanical stresses, enabling the bone tissue to gradually fill the empty space. The most preferable solution is to have an implant undergoing resorption over time, thus enabling the entire space to be filled with new bone tissue. Another criterion is ensuring the flow of nutrients and cells in the bloodstream trough the scaffolds material. Also some modifications to the implant surfaces are used to accelerate the regeneration of substantial loss of the tissue.

In the effectiveness of the bone implant use the surface layers of an implant containing calcium phosphates play an important role. The natural bone in up to 70% (depending on the type of bone tissue) consists of an inorganic matter, largely composed of hydroxyapatite deposited in a form of crystals. Hydroxyapatite $Ca_{10}(PO_4)_6(OH)_2$ is one of the major minerals in the human body. It is responsible for the hardness and strength of bones and teeth. In the human body hydroxyapatite occurs in a form of crystals with lamellar structure, 2 nm thick, 25 nm wide, and 50 nm long. [M. Sadat-Shojai, M.-T. Khorasani, E. Dinpanah-Khoshdargi, A. Jamshidi "*Synthesis methods for nanosized hydroxyapatite with diverse structures*", Acta Biomaterialia, Vol. 9, 2013, pp. 7591-7621]. Hydroxyapatite is a material widely used in orthopaedics, maxillofacial and implant surgeries, inter alia, for the production of layers of implants aimed at bone regeneration.

New potential for facilitation or accelerating the regeneration of bone tissue lays in the nanotechnology, the field in which properties of the known materials change in a surprising manner along with the change of the material size, ranging from 1 to 100 nm.

Publication WO2011/022642 discloses coating of bone implants with a porous layer composed of hydroxyapatite and zinc dioxide, having a size exceeding 50 nm.

Publication WO2013/112743 describes an implant with islands of hydroxyapatite having an average thickness of 45-70 nm, albeit an information about the size of hydroxyapatite nano-particles and the molar ratio of calcium to phosphorus has been given.

In U.S. Pat. No. 6,129,928 patent specification have been presented layers of calcium phosphate of undetermined nano-structure and thickness of 2-30 µm, applied to metallic implants. The disadvantages of the method for covering implants disclosed there are complex multi-stage manufacturing process and a considerable thickness of the layers obtained.

In U.S. Pat. No. 5,441,536 patent specification is disclosed a method for producing hydroxyapatite layers on medical implants by hydrothermal treatment in temperatures higher than 100° C., however the resulting structure of layers obtained is not specified in this patent. The coating obtained by this method is characterized by the average thickness of 50 µm and tendency for delaminating when under stress. Publication WO2002/078759 describes a bioactive layer consisting of the various phases of calcium-phosphate. The composition of this layer consists of amorphous and nano-crystalline calcium phosphates forming a porous layer, having a thickness of 0.1 to 50 µm and a density of pores ranging from $10^4$ to $10^8/mm^2$. Such a layer may be a source of calcium ions needed for the active bone formation. The ratio of calcium to phosphorus over the entire surface of the sub-structure ranges from 0.5 to 2. The disadvantage of the described method is the need for forming pores in the layer. In the publication the presence in the layer of nano-crystalline hydroxyapatite is mentioned, however, very important data in terms of nanotechnology, such as the size and distribution of crystallite and its structure, are not given. In addition, calcium phosphate and hydroxyapatite represent only 1 to 40% of the coating. There is also no information on the coating of porous scaffolds.

Publication CN101703798 discloses coating facilitated by electrostatic discharges. Thus obtained layer consists of a nano-particles of hydroxyapatite in an amount ranging from 70 to 90% and the additive of silk fibres in an amount from 10 to 30% by weight. However, neither layer thickness nor its structure has been specified. Publication US2011/0281127 discloses a method of manufacturing a hydroxyapatite layer having a thickness of 30 to 50 nm. An optimal biocompatibility, confirmed in cellular assays, has been shown in the layers consisting of particles having a diameter of less than 50 nm, preferably 30 nm. However, the actual effectiveness of such layers has not been specified.

In the review article "*Calcium phosphate coatings for bio-implant applications: Materials, performance factors, and Methodologies*" [Materials Science and Engineering R 66 (2009) 1-70] S. R. Paital and N. Dahore describe various methods for production of layers of calcium phosphate on implants for bone regeneration, especially metal ones, particularly made of titanium alloys. This publication discloses, among other things, various kinds of deposition from vapour phase of PVD family (Physical Vapour Deposition) or CVD family (Chemical Vapour Deposition), for example, IBAD method (Ion Beam Assisted Deposition) using ion beam. Described there are also processes of plasma spraying (Plasma Spray Deposition), PLD laser technologies (Pulsed Laser Deposition), electrophoretic deposition, electrochemical surface treatment, e.g. MAO (Micro-arc oxidation), spray deposition of atoms/ions in a magnetic field (Magnetron Sputtering Deposition), direct laser melting method, a sol-gel method and also the production of solutions simulating physiological fluids (Simulated Body Fluid, SBF). A lot of these methods can only be used to produce layers on materials resistant to temperatures above 200° C., thus precluding the use of this methods for most plastics. Of above mentioned methods only PVD, sol-gel and SBF can be used at temperatures below 200° C. In the case of the latter two methods further activation of the surface materials is required to enable the subsequent process of nucleation to run more efficiently, and to strengthen the connection between the substructure and hydroxyapatite.

An example of implementation of the method of plasma spraying to coat the implant made of plastic is disclosed in publication WO2012/110816. This method involves the formation of the transition layer, for example titanium one, and then deposition of the further layer of polymeric material or ceramic material, for example hydroxyapatite. The substructure material must be resistant to temperatures above 200-250° C. (e.g. PEEK, PAEK, polyamide). The outer layer of the hydroxyapatite can be applied by plasma spraying or by electroplating. The advantage of this method is the good adhesion of the layers to the substructure, but its disadvantage is the need for the transition metal layer and the process temperature greater than 200° C. No information on the structure and thickness of this layer has been specified.

Another method for producing a hydroxyapatite layer is called "layer by layer" method (LBL). Using this method the composite was made, consisting of layers, arranged in turns, of chitosan with hydroxyapatite and of polyacrylic acid (PAA).

This method is disclosed in N. Shah, J. Hong et al. "Osteophilic multilayer coatings for accelerated bone tissue growth" [Adv Mater. May 15, 2012; 24 (11): pp. 1445-50], wherein the further layer is applied containing growth factors, such as rhBMP-2. The advantage of this method lays in obtaining a homogeneous layer containing various types of active substances. The process is carried out at room temperature. For application on industrial scale the multiply immersing of the material in a suspension is necessary. This extends the duration of the process and increases the possibility of introducing contamination. In the paper "The future of biological coatings for orthopaedic implants" [Biomaterials Vol. 34, Issue 13 Apr. 2013, pp. 3174-3183] S. Goodman and Z. Yao reveal the problem of insufficient mechanic resistance of such a layer in terms of its adhesion to the substructure. The publication of A. Oyane, C. Choong, J. Triffitt "Simple surface modification of poly (ε caprolactone) for apatite deposition from simulated body fluid" [Biomaterials, Vol. 26, Issue 15 May 2005, pp. 2407-2413] describes a method of producing layers of O-hydroxyapatite by its precipitation in a solution stimulating fluids of the human body. The material being coated is a scaffold of polycaprolactone (PCL), made using three-dimensional printing technique (Fused Deposition Modeling, FDM). Additionally, the scaffold was immersed in SBF for 14 days, during which calcium phosphate layer grew. The layer obtained consisted of hydroxyapatite. A similar technique is described in the paper of T. Kokubo "Formation of biologically active bone-like apatite on polymers and metals by a Biomimetic process" [Thermochimica Acta, Vol. 280-281, July 1996, pp. 479-490]. The disadvantage of this method is a length of the process, as well as weak binding between the polymer and the ceramics. On SEM micrographs the cracks and defects of the layer are shown in a place where the layer detached itself from the substructure. Implementation of the same method discloses patent specification U.S. Pat. No. 8,075,562. The method presented regards obtaining the layers on the substructure by immersing the polymeric material for the coating in solution of simulating physiological fluids (SBF) with the addition of bone growth factors, for example the e-BMP-2 and a ready implant in the form of a polymer screw coated with a layer of hydroxyapatite. The disclosed technology provides a homogeneous layer, which contains chemically bound hydroxyapatite and growth factors. The drawback of this technology is the necessity of immersing the coated material in a number of different solutions and a long time needed for layer preparation. No information about the structure of the nano-particles and layers has been specified.

Publication EP2251049 discloses a method of producing on a metal substructure a hydroxyapatite layer, which consists of collagen, calcium phosphate (hydroxy-apatite) and optionally some growth factors. According to this method, the metal substructure intended for coating is inserted into a liquid containing collagen or is coated with such liquid droplets. Followed by removal of excess collagen and immersing the substructure in a metastable solution containing calcium and phosphate ions that results in precipitation of calcium phosphates. The disadvantage of this solution is the long time needed for preparing the coating, at least 12 hours of soaking in a solution of calcium and phosphate ions, two hours of freezing and lyophilisation step taking several hours. Here, too, no information about the structure of the layers and particles has been given.

A similar technology discloses patent specification U.S. Pat. No. 6,280,789. It presents the production of hydroxyapatite coatings on the surface of metallic and ceramic implants. The substructure material is dipped in a solution containing calcium, phosphate and bicarbonate, at a pH in the range of 6.8 to 8. The solution is heated to a temperature between 50 and 80° C., resulting in an increase of pH and precipitation of hydroxyapatite with addition of hydrogencarbonate ions. The precipitated crystallites of hydroxyapatite have a length of 10 to 40 nm and a width of 3 to 10 nm. The advantage of this method is a short duration of the process, however a relatively high process temperature of this method makes it unsuitable for polymer substructures, particularly those with low softening temperature and poor chemical resistance.

Technologies for producing layers using energy of ultrasounds are also known. Patent specification U.S. Pat. No. 7,896,539 discloses coating with drugs or polymers of stents (implants restoring the patency of blood vessels) using an ultrasonic nozzle for spraying the coating material. There is, however, no possibility of a uniform coating of porous substructures, and possibility of coating with nano-particles of hydroxy-apatite has not been even suggested.

In publication WO2007/127193 the preparation of layers on the surface of medical implants by electrostatic applying of the spray material is described. However, this methods is limited only to coating conductive materials or materials covered with pre-added conductive layer. In addition, it is difficult or impossible to cover the whole volume of the material with a small size of the pores and a complicated geometry. Not even a suggestion of the possibility of coating with nano-particles of hydroxyapatite has been given.

A lot of the plastic materials used as implants for bone tissue regeneration are thermoplastic materials, which can be shaped with the extrusion moulding or injection. The temperatures at which such materials can be formed are often in the region of 100° C. or even lower. For example, polycaprolactone softening point is c.a. 60° C. For this reason, the process of applying the layer of such a material on an implant requires temperatures below the softening temperatures to prevent distortion or damage. Publication US2011/097957 describes a method of ultrasonic applying of metal oxides (CuO, ZnO, MgO) on fabric, in order to impart antibacterial properties, while publication US2011/300767 discloses a method of ultrasonic adhering to the fabric of the protein microspheres containing some substance, e.g. drug, which is then released into the environment. Both publications do not contain any teachings regarding covering of the bone implants with hydroxyapatite.

Publication JP2013022234 discloses a method for obtaining a hydroxyapatite layer on a substructure of thermoplastic material by applying on the substructure the hydroxyapatite particles which blend into the material after heating above the softening temperature. Effectiveness of the coating is checked by subjecting the coating to ultrasound at a frequency of 38 KHz for a period of 10 minutes; what is worth noting is that ultrasounds used here are not used in the coating process. No information about the nano-structure of hydroxyapatite used has been given.

Publication KR101005499 discloses a method of surface hardening of three dimensional stents and application of medicinal substances on their surface by ultrasonic cavitation in a liquid in which the stent is immersed. Also in this solution, there are no guidelines as to the use of ultrasound for obtaining hydroxyapatite layers.

The Polish patent application P.396906 discloses a synthetic nano-lamella of hydroxyapatite with a hexagonal structure and having an average particle size ranging from 3 to 30 nm. The molar ratio of calcium to phosphorus (Ca/P) of this nano-lamella ranges from 1.55 to 1.65. Disclosed nano-powder is intended for filling undesirable cavities in bone tissue, but in the said application there are no guidelines as to the application of such a nano-powder in the production of implants and implant layers.

The Polish patent application P.399701 discloses a bone implant formed of, a compacted under high pressure, nano-powder of synthetic hydroxyapatite, having a hexagonal structure with an average particle size from 3 to 30 nm and a specific surface area greater than 200 m$^2$/g. This report does not contain any guidance on durable coating with the powder of spatially complex bone implants, especially ones with high flexibility.

The publication of I. Salma et al., "*First results of the bone tissue morphological evaluation after implantation of new polymer and tricalcium phosphate scaffolds coated with resorbable nano hydroxyapatite*" [Journal of Tissue Engineering and Regenerative Medicine 8, 409-410] discloses test results of coating porous scaffolds with nano hydroxyapatite using ultrasounds. However, this publication does not disclose any details of the coating and the obtained coating properties, while it is well known that in nanotechnology the properties of the nano-particles strongly depend on their size, shape, chemical composition of molecules attached to their surfaces and their inner structure.

In their publication "*Ultrasonic coating technique of a polymer scaffold for bone implant applications*" [European Cells and Materials, Vol. 26, Suppl. 2, 2013, p. 17] A. Kępdzierska et al. describe scaffolds for bone tissue regeneration made by deposition on the polymer scaffolds the layers of nano-hydroxyapatite, with lamellar structure and size from 5 to 30 nm, using ultrasounds. This publication does not contain information regarding the chemical composition of the hydroxyapatite used and kinds of physical phenomena occurring during the sonication, and the possible impact of the structure obtained on the regeneration processes of bone tissue. It is very important as these phenomena, as every specialists involved in the processes that occur when the size of the particles of matter is less than 100 nm is aware, are very unpredictable and strongly depend on the size of nano-structures; as the same, from the chemical and physical point of view, material with the particles size of 70 nm can have fundamentally different properties than a material with the particles size of 20 nm.

DISCLOSURE OF INVENTION

The aim of the invention is to obtain an efficient bone implant stimulating bone growth and the fast and simple method of manufaturing such implants.

This aim is to be achieved by the method according to the invention consising on depositing a synthetic hydroxyapatite on a supporting structure by immersing the supporting structure in a liquid being a source of this hydroxyapatite. It characterized in that the supporting structure of the implant is first immersed in a suspension consisting of a liquid phase, advantageously water, containing a disphersed phase of synthetic hydroxyapatite particles having an average particle size not greater than 100 nm, advantageously not greater than 30 nm. Next, in a portion of the suspension being in contact with the supporting structure cavitation is induced.

In one of embodiments of the method according to the invention for the preparation of the dispersed phase are used the hydroxyapatite particles containing structural water in an amount from 2 to 6% by weight.

In another embodiment of the method according to the invention molar ratio of calcium to phosphorus (Ca/P) of the hydroxyapatite particles is greater than 1.55 and less than 1.67.

In another embodiment of the method according to the invention the cavitation is induced by means of an object immersed into the suspension near the supporting structure of the implant and having vibrations induced at a frequency ranging from 18 to 40 kHz, advantageously at frequency of 20 kHz.

In another embodiment of the method according to the invention the object immersed in the suspension has a vibrating front surface and wherein during inducement of the cavitation state the distance of the front surface of this object from the surface of the supporting structure is not greater than 200% of the front surface diameter, advantageously about 100% of that diameter.

In another embodiment of the method according to the invention weight ratio of the dispersed phase of the suspension (3) is from 0.01% to 2%, advantageously from 0.1% to 0.5%.

In another embodiment of the method according to the invention temperature of the suspension does not exceed 100° C., advantageously does not exceed 40° C.

In yet another embodiment of the method according to the invention duration of the cavitation state ranges from 1 minute to 30 minutes and advantageously does not exceed 15 minutes.

Implant according to the invention has a supporting structure at least partially coated with a synthetic hydroxyapatite. It characterized in that the synthetic hydroxyapatite coating the supporting structure is in the form of particles having an average particle size grater 100 nm, advantageously not greater than 30 nm, subjected to cavitation, advantageously ultrasonic. Thickness of this coating is from 50 nm to 1000 nm, advantageously from 50 nm to 300 nm.

In one of embodiments of the implant according to the invention the hydroxyapatite particles contain structural water in the amount from 2% to 6% by weight.

In another embodiment of the implant according to the invention molar ratio of calcium to phosphorus (Ca/P) of the hydroxyapatite particles is greater than 1.55 and less than 1.67.

In another embodiment of the implant according to the invention the coating covers at least 50% of the supporting structure.

In another embodiment of the implant according to the invention the supporting structure is made of a polymeric material or of a ceramic material.

In another embodiment of the implant according to the invention the supporting structure is made of polymeric material having a porosity raging from 40% to 80% and it can be made of polymeric fibers.

In yet another embodiment of the implant according to the invention the supporting structure is made of ceramic material and is characterized by structural microporosity in the range from 25% to 75%, advantageously ammounting 50%.

The ceramic supporting structure of the implant can be made of beta-tricalcium phosphate (β-TCP).

Implant according to the invention can be manufactured by the described above method according to the invention.

The implant according to the invention is coated with a hydroxyapatite which very effectively stimulates cell proliferation and an bone tissue growth in the body. The results from in vivo test with rabbits indicate that at least 25% of the pores of such an implant and at least 10% by volume of bone loss is filled with new bone tissue three months after implantation. This tissue builds up evenly and is characterized with a good quality seen in its protein content, its cell activity and bone growth factors, indices of tissue distribution and their inhibitors, as well as pro- and anti-inflammatory cytokines. The durability of the applied coating of hydroxyapatite, using the method of the present invention, even to a not resistant supporting structure of the implant, facilitates adjustment of the implants shape, for example by cutting or bending already during the operation, without losing the beneficial surface properties.

Manufacturing of an implant by a method according to the invention also allows one for significant savings due to its short duration (less than 60 minutes) and the low process temperature (below 100° C.), as well as the possibility of using a suspension having low concentration of hydroxyapatite. The low process temperature dramatically extends the range of suitable materials from which supporting structure of the implant can be made, in particular materials having low melting point, up till now not suitable for such purposes.

BRIEF DESCRIPTION OF DRAWINGS

The examplary embodiments of the invention are shown on the drawings, in which

FIG. 3 shows a SEM image of the uncoated polymer supporting structure from the first example in the in vivo tests, while FIG. 6 shows a microscopic image of the ceramic supporting structure of the second embodiment after the in vivo test, while

MODE FOR CARRYING OUT INVENTION

The invention will be described in further detail in the following exemplary embodiments. In these examples a nano-powder of hydroxyapatite was used, under the trade name GoHAP, having the following characteristics:

the nano-powder particles are in a form of platelets having an average particle size less than 30 nm, as based on the analysis of the image obtained by the transmission electron microscope (TEM) using dark-field for at least 200 particles, wherein the average particle size equals the diameter of the circle drawn around the particle shape;

ratio of calcium to phosphorus (Ca/P) is greater than 1.55, but smaller than 1.67;

the nano-powder contains structural water in an amount ranging from 2 to 6% by weight, wherein the amount of the water is determined by the weight loss of the nano-powder during the heating above 200° C.;

solubility, determined by the procedure of ISO 10993-14, ranging from 5 to 35 mg/dm$^3$.

EXAMPLE 1

Porous Polymer Implant

Figure 1:
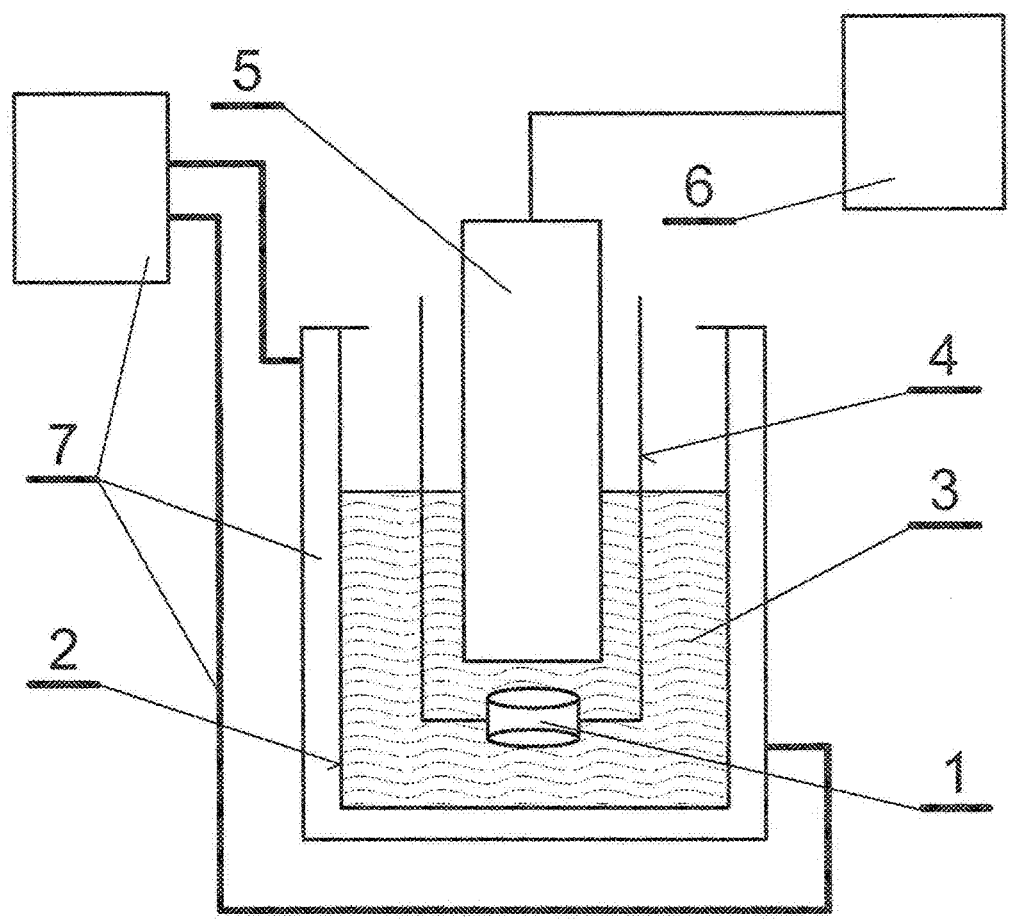
FIG. 1 is a diagram of an exemplary working-stand for covering an implant supporting structure with hydroxyapatite.
Figure 2:
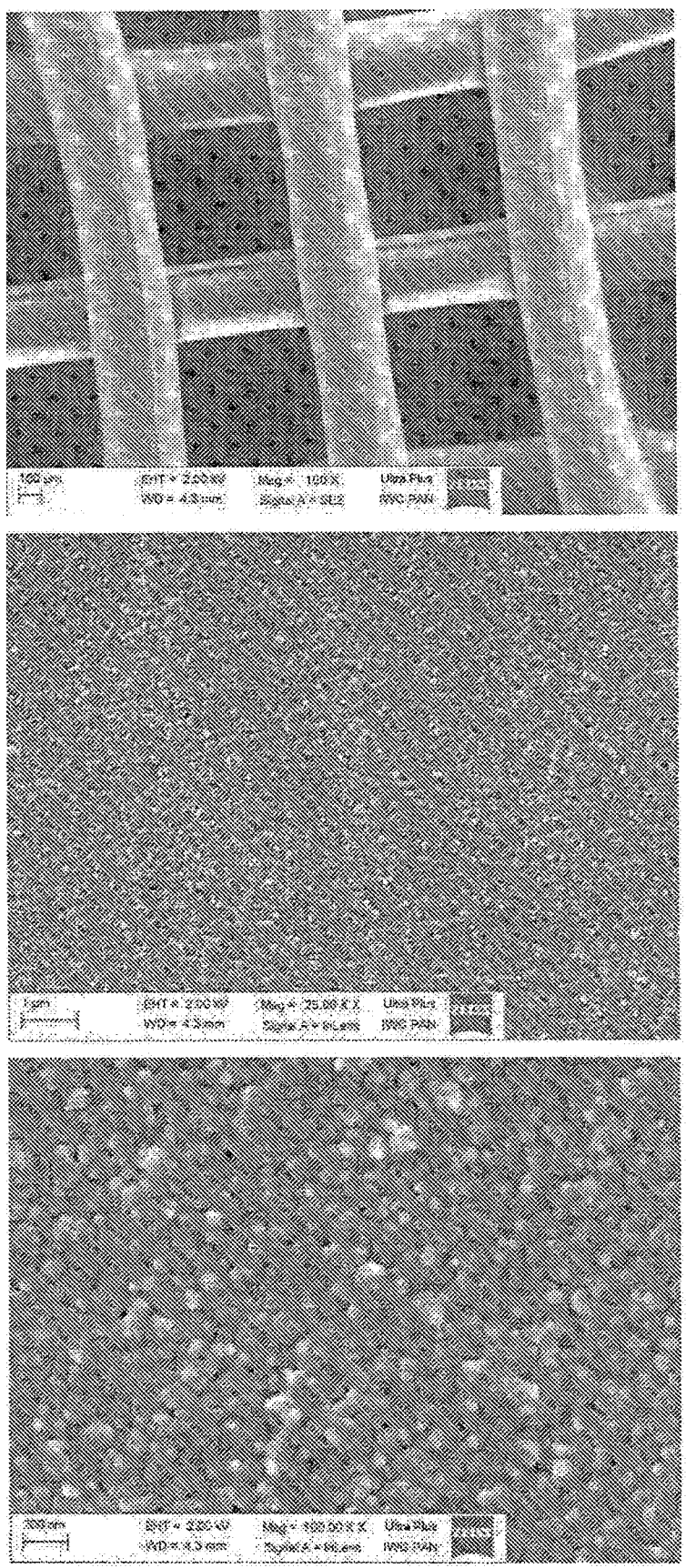
FIG. 2 shows a microscope images (SEM) of the implant from the first embodiment in three different magnifications.

Supporting structure 1 of the implant was made of biodegradable polymer-poly-caprolactone (PCL). It has a form of 3-dimensional scaffold, measuring 4×6 mm, made from polymer fibers by printing technology of the spatial "rapid prototyping" which is described in W. Święszkowski et al., "*Repair and regeneration of ostechondral defects in the articular joints*" [Biomolecular Engineering, 2007 24 (5): pp. 489-95] The supporting structure 1 is characterized by the porosity of approx. 41%. As the coating material of the supporting structure a nano-powder of hydroxyapatite GoHAP was used, with a molar ratio (Ca/P) of 1.65, containing 5% by weight of structural water. This powder (in amount of 0.1% by weight) was mixed in 50 ml vessel 2 with deionized water to form a homogeneous suspension 3, wherein the external phase is water and the internal phase is hydroxyapatite. The supporting structure 1 was rinsed with distilled water, and then fitted to the stand 4 for immobilization. The stand 4 was placed in the vessel 2 with the suspension 3 heated to 30° C. An ultrasound head 5 with the front (emitting) surface having a diameter of 13 mm, being a source of ultrasounds, was connected to an power supply device 6 and immersed in the suspension 3. The distance from the front surface of the head 5 and the supporting structure 1 shall not be larger than 200% of the diameter of this head's surface, wherein the optimum is to keep a distance equal to 100% of its diameter. For the following fifteen minutes the head 5 generated ultrasounds at a frequency of 20 kHz. The generated ultrasound of this frequency induced a phenomenon of ultrasound cavitation, i.e. formation and activity of gas bubbles in the liquid exposed to the ultrasonic field. Cavitation occurred mainly in the portion of the suspension 3 being in contact with the surface of the supporting structure 1, including the suspension 3 filling the pores of the supporting structure 1. The cavitation was confirmed by the observation of the liquid and temperature monitoring. In order to maintain a stable temperature of the suspension 3 a flow cooling circuit 7 was used. When the power supply of the head 4 was turned off the coated implant 1 was taken out of the vessel 2, rinsed with distilled water, and then dried in laminar flow cabinet of high purity. These steps were repeated dozen times to obtain the number of implants sufficient for in vitro and in vivo tests. Based on the SEM image analysis it was found that GoHAP layer applied on the supporting structure 1 has a morphological features similar to that of the initial GoHAP powder (size, particle shape). The coating was obtained, having a thickness of 200 nm uniformly covering more than 85% of the supporting structure surface of implant 1 (FIG. 2).

The obtained implants were firstly used in cellular assays in vitro tests. The cell line MG-63 (osteosarcoma) and D-MEM culture medium supplemented with 10% FBS was used. In addition to the cell medium for the above samples penicillin/streptomycin was added. The incubation was carried out on 24 well plates at 37° C. and 5% $CO_2$ environment. The cells were separated from the incubation substrate with 0.25% trypsin/EDTA. Implants (scaffold) for testing were rinsed with PBS (phosphate buffer saline, pH 7.4). Then cells were planted on the prepared scaffolds. For each tested scaffold concentration of approx 105 cells in 200 ml culture medium were used and then scaffolds were placed in the incubator for one and a half hours. After this time, the medium was added to the wells in order to completely cover the sample. Afterwards, the incubation lasted for five days. The results showed that cell proliferation on the polymer scaffold with GoHAP layer is higher than on the corresponding polymer scaffold without such a layer. Analysis of the number of cells clearly showed that the polymer scaffold with GoHAP layer has better features for stimulating cell proliferation. After five days of culture, the cell density on the polymer scaffold with such a layer was three times higher than on the polymer scaffold without a coating. After five days of culture duration, on the inverted microscope it was noted that the confluence of cells in all wells around the test material was ≥95%.

Figure 3:
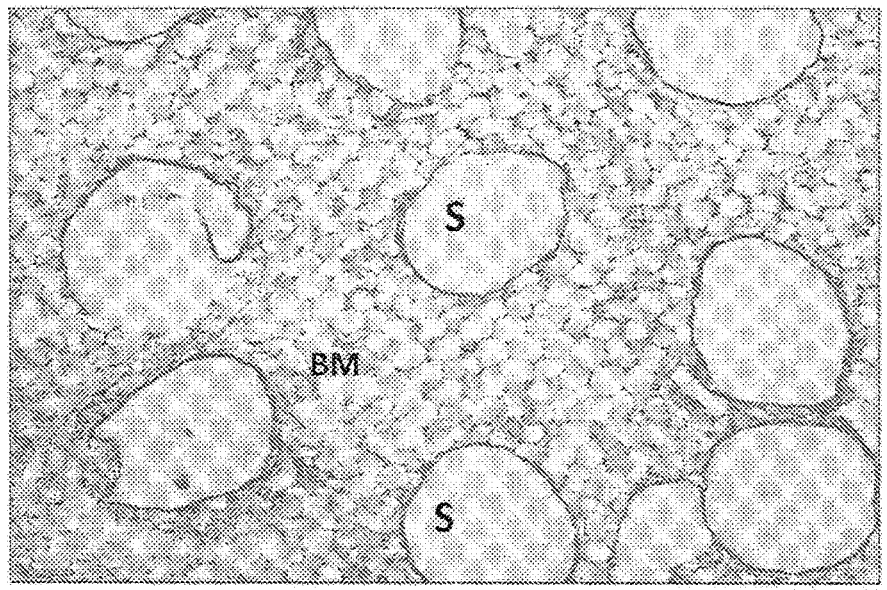
Figure 4:
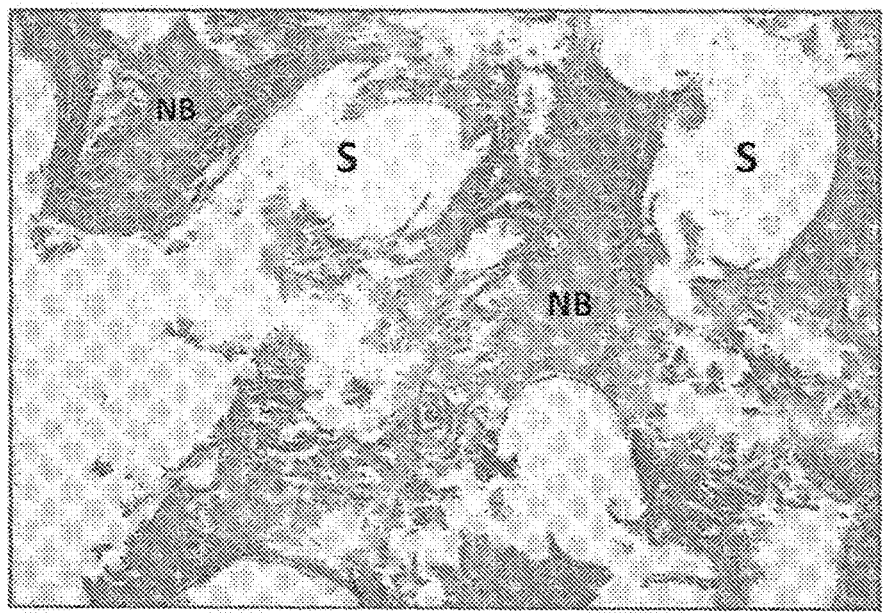
FIG. 4 shows a microscope image of the implant with the supporting structure coated with GoHAP in the similar test using animal model.

The implants prepared in this embodiment were also examined in vivo using an animal model. A ten-month old, male, New Zealand rabbits were given, using standard procedures, a general anesthetic and in this state in their tibia bone holes were made that were filled with implants mentioned. As reference material the clean polymer scaffolds described above were used for filling the holes in the hip bone of individuals from the control group. Upon completion of implantation periosteum of all animals was sutured and soft tissue was closed layer by layer with 5-0 Vicryl sutures. The skin was stitched using interruptible 4-0 Prolene sutures. The subcutaneous injection of the antibiotic solution Enrobioflox 5% (50 mg/ml solution) were applied once a day for 5 days, containing 5 mg per kilograms of weight of the active substance Enrofloxacin. After three months, euthanasia, using standard procedures, of all study subjects was carried out, after which the hard and soft tissue samples were collected and examined regarding their histology and capacity for facilitating bone regeneration. Routine staining with hematoxylin and eosin was performed in each case. The extracted polymer scaffold without a hydroxyapatite layer is shown in section in the FIG. 3, where there is a space for the red marrow (BM) penetration around the fibers (S) of the pure scaffold. FIG. 4 shows the new bone (NB) filling the spaces between the residues of the fibers (S) of the implant according to the invention. Morphometric analysis of the image of FIG. 4 indicated that the proportion of new tissue in the porous space of the implant with GoHAP layer amounted to approx. 33%, of which 35% was constituted by the new bone tissue (NB), whereas for a scaffold (S) without the such layer bone tissue growth was negligible.

EXAMPLE 2

Porous Ceramic Implant

Figure 5:
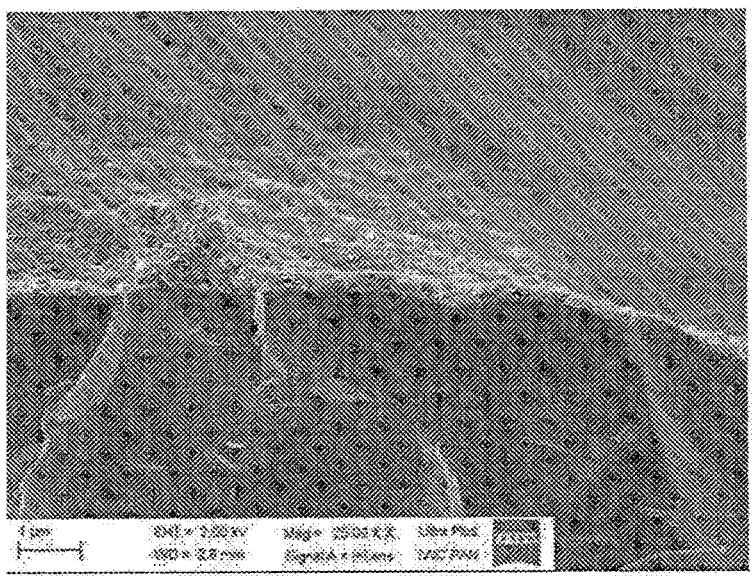
FIG. 5 shows microscope images (SEM) of the implant from the second embodiment in three different magnifications.
Figure 5:
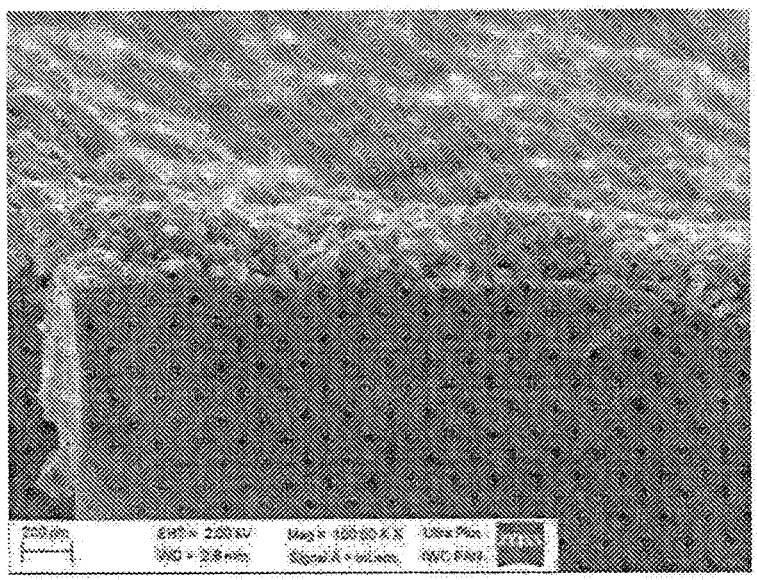
Figure 5:
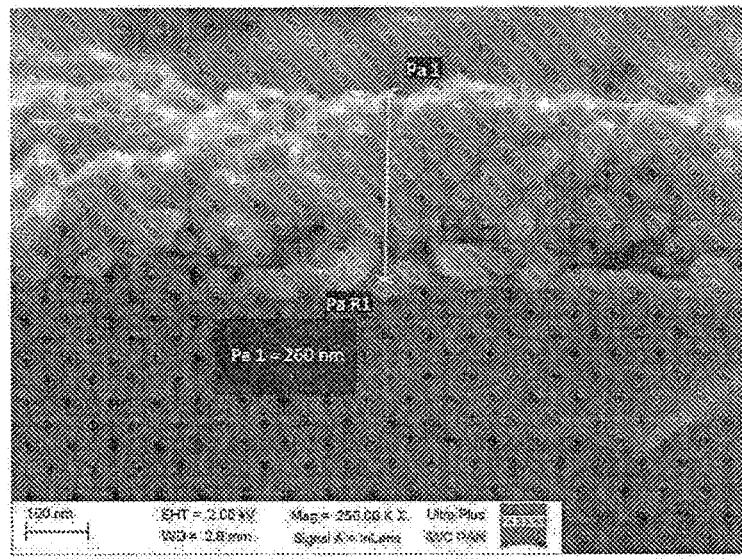

In order to produce a ceramic implant coated with a layer of nano-particles of hydroxyapatite a supporting structure in a form of porous ceramic pellets was used. For the production of pellets a method of uniaxial pressing of the β-TCP powder was used with a pressure force of 15 kN. For the production of one sample 3.06 g of powder was taken. In order to achieve structural microporosity a heat treatment method was used in which said pallet was subjected to 1200° C. for a period of two hours. The pellets were then examined for signs of porosity using methods of computer microtomography and Archimedes method. According to the μ-CT calculations a porosity of 49% was reached, while the result of the analysis by the Archimedes method was 52% (+/− 2.6%). The coating processes with GoHAP of the prepared ceramic implant supporting structure was carried out in a manner analogous to the first example, wherein a nano-powder with a water content of 5% by weight was used. Obtained coating had the thickness of 250 nm, uniformly covering more than 80% of the surface of the supporting structure (1) of the implant (FIG. 5). The material used for coating, i.e. GoHAP nano-powder of hydroxyapatite was characterized by a molar ratio (Ca/P) of 1.66.

Figure 6:
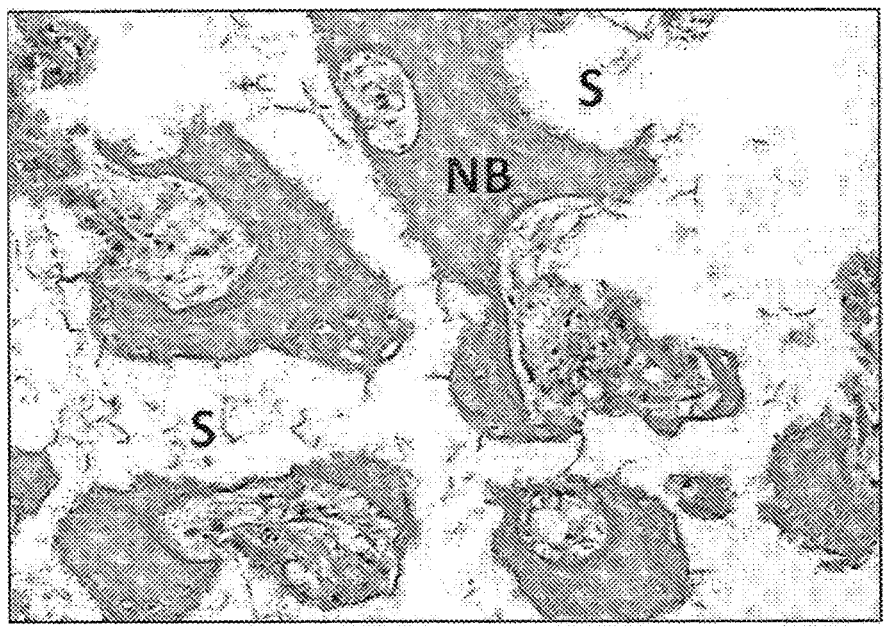
Figure 7:
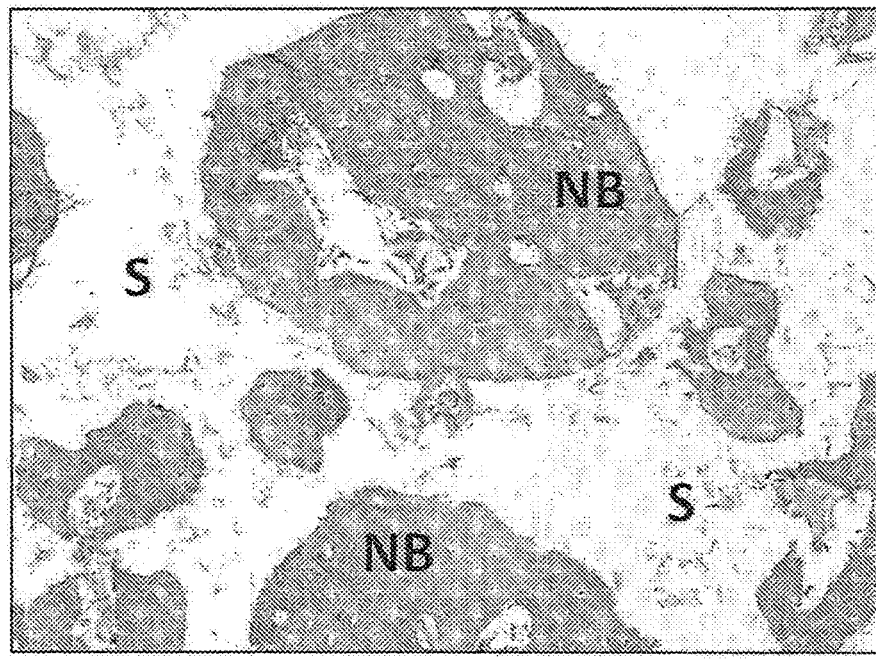
FIG. 7 shows a microscope image of such an implant with the supporting structure coated with GoHAP after similar in vivo test.

The ceramic layer on GoHAP implants was tested in vivo using an animal model (New Zealand rabbits). The procedure of implanting ceramic implant, the used comparative material, the collection of samples for testing and hematoxylin and eosin staining were performed similarly as in the first example. The extracted after three months ceramic scaffolds without GoHAP layer have been substantially filled with bone tissue (NB in FIG. 6). An morphometric analysis of these structures images showed that almost 50% of the implant (scaffold) pores were filled with the bone tissue. Morphometric analysis of the image of the ceramic scaffold with a layer of GoHAP, presented at FIG. 7, showed that almost 70% of the scaffold pores were filled with the bone tissue.

EXAMPLE 3

Monolithic Metallic Implant

Figure 8:
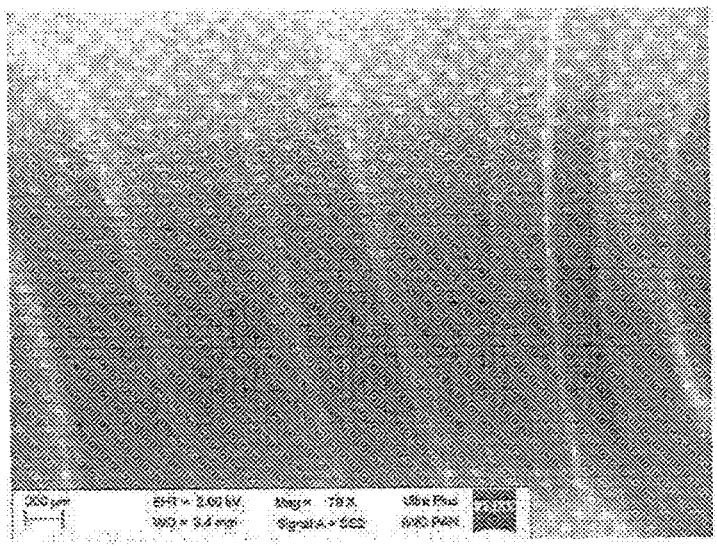
FIG. 8 shows microscope images (SEM) of the implant from the third embodiment in three different magnifications.
Figure 8:
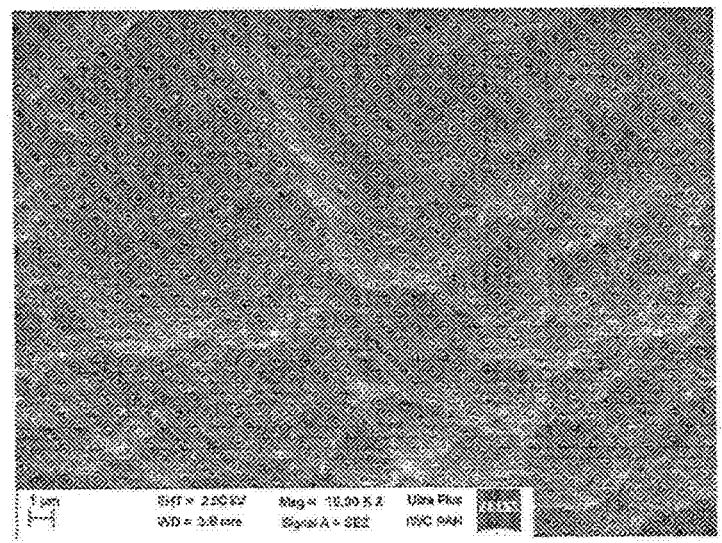
Figure 8:
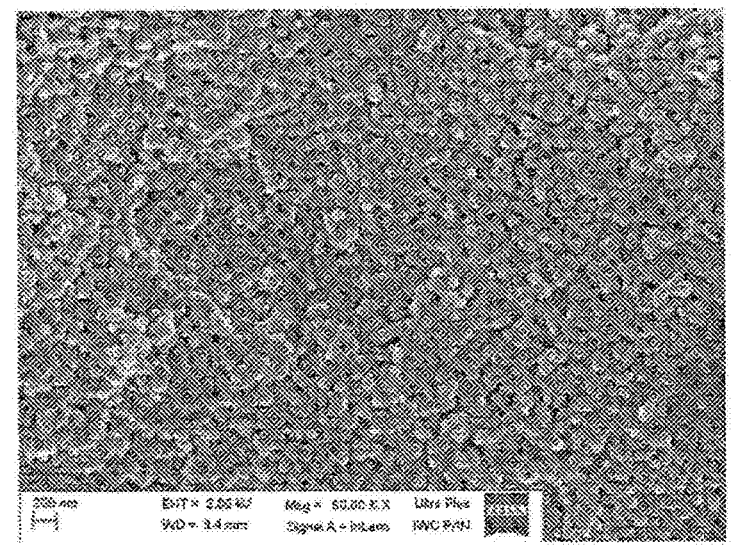

In order to produce a monolithic metal implant a supporting structure was used in a form of a titanium screw having a diameter of 5 mm and a length of 150 mm, dedicated to arthroscopy. The screw was coated with a layer of GoHAP nano-particles by ultrasonic effect on the aqueous suspensions described in detail in the first embodiment, wherein a powder has a diameter of not more than 6 nm, a structural water content of 3% by weight, molar ratio of calcium to phosphorus (Ca/P) of 1.60. Based on the SEM image analysis it was found that the resulting coating has morphological properties characteristic for the initial GoHAP powder. The titanium screw was coated with a uniform layer of hydroxyapatite having a thickness of 200 nm, covering 85% of its surface (FIG. 8).

The invention claimed is:

1. A method for manufacturing a bone regeneration implant, consisting of depositing a synthetic hydroxyapatite on a supporting structure, having a step of immersing the supporting structure in a suspension consisting of a liquid phase, containing a dispersed phase of synthetic hydroxyapatite particles having an average particle size not greater than 100 nm and molar ratio of calcium to phosphorus (Ca/P) greater than 1.55 and less than 1.67, and a step of inducing a ultrasonic cavitation in a portion of the suspension being in contact with the supporting structure, characterized in that for preparation of the dispersed phase are used the hydroxyapatite particles containing structural water in an amount from 2 to 6% by weight, the supporting structure is immobilized in the suspension, the ultrasonic cavitation is induced by means of an vibrating object immersed into the suspension near the immobilized supporting structure of the implant, the vibrating object has a vibrating front surface, and during the cavitation the distance of the vibrating front surface from the surface of the supporting structure is constant and not greater than 200% of the vibrating front surface diameter.

2. The method according to claim 1, wherein the weight ratio of synthetic hydroxyapatite in the dispersed phase of the suspension is from 0.1% to 0.5% by weight.

3. The method according, to claim 2, wherein the duration of the cavitation state ranges from 1 minute to 30 minutes.

4. A bone regeneration implant having a supporting structure at least partially coated with a synthetic hydroxyapatite particles which were subjected to ultrasound cavitation, the particles have an average size not greater than 100 nm, and molar ratio of calcium to phosphorus (Ca/P) in the particles is greater than 1.55 and less than 1.67, whereas the thickness of this coating is from 50 nm to 300 nm, characterized in that the hydroxyapatite particles contain structural water in the amount from 2% to 6% by weight, the coating covers at least 80% of the supporting structure.

5. The implant according to claim 4, wherein the supporting structure is made of polymeric fibers.

6. The implant according to claim 4, wherein the supporting structure is made of beta-tricalcium phosphate ($\beta$-TCP).

7. The method according to claim 1, wherein the liquid phase of the suspension is water.

8. The method according to claim 7, wherein the weight ratio of the dispersed phase in the suspension is from 0.1% to 0.5% by weight.

9. The method according, to claim 3, wherein duration of the cavitation state does not exceed 15 minutes.

10. The method according, to claim 3, wherein duration of the cavitation state ranges from 1 minute to 30 minutes.

* * * * *